(12) United States Patent
Simcock et al.

(10) Patent No.: US 9,097,649 B2
(45) Date of Patent: Aug. 4, 2015

(54) OPTICAL DESIGN TECHNIQUES FOR PROVIDING FAVORABLE FABRICATION CHARACTERISTICS

(71) Applicant: Halliburton Energy Services, Inc., Houston, TX (US)

(72) Inventors: Michael Neil Simcock, Columbia, SC (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/232,039

(22) PCT Filed: Feb. 20, 2013

(86) PCT No.: PCT/US2013/026894
§ 371 (c)(1),
(2) Date: Jan. 10, 2014

(87) PCT Pub. No.: WO2014/130026
PCT Pub. Date: Aug. 28, 2014

(65) Prior Publication Data
US 2014/0255598 A1    Sep. 11, 2014

(51) Int. Cl.
*G01N 21/25* (2006.01)
(52) U.S. Cl.
CPC .................... *G01N 21/255* (2013.01)
(58) Field of Classification Search
CPC .................................................. G01N 21/255
USPC ................................................ 427/9, 10, 162
See application file for complete search history.

(56) References Cited

U.S. PATENT DOCUMENTS

| | | | |
|---|---|---|---|
| 6,198,531 B1 | 3/2001 | Myrick et al. | |
| 6,529,276 B1 | 3/2003 | Myrick | |
| 7,138,156 B1 * | 11/2006 | Myrick et al. | 427/10 |
| 7,920,258 B2 | 4/2011 | Myrick et al. | |
| 8,352,205 B2 | 1/2013 | Myrick et al. | |
| 2010/0221762 A1 | 9/2010 | Sterling et al. | |

OTHER PUBLICATIONS

On-line reoptimization of filter designs for multivariate optical elements Haibach et al, Applied Optics vol. 42 No. 10, pp. 1833-1838, Apr. 2003.*

(Continued)

*Primary Examiner* — Alex A Rolland
(74) *Attorney, Agent, or Firm* — McDermott Will & Emery LLP; Benjamin Fite

(57) ABSTRACT

Disclosed are methods and techniques for providing favorable fabrication characteristics for optical elements. One method includes providing a desired integrated computational element (ICE) design comprising a plurality of layers, each layer having a design thickness, randomizing the design thickness of each layer of the desired ICE design to simulate a fabrication error in each layer, thereby generating a plurality of randomized ICE designs, calculating a standard error of calibration between each randomized ICE design and the desired ICE design, correlating the standard error of calibration between a given layer of the desired ICE design and the fabrication error of each corresponding layer of each randomized ICE design, and ranking the plurality of layers of the desired ICE design based on the sensitivity to changes in the standard error of calibration.

23 Claims, 2 Drawing Sheets

(56) References Cited

OTHER PUBLICATIONS

International Search Report and Written Opinion for PCT/US2013/026894 dated Nov. 27, 2013.
Profeta et al., "Spectral Resolution in Multivariate Optical Computing," Spectrochimica Acta Part A 67, 2007, pp. 483-502.
Haibach et al., "On-Line Optimization of Filter Designs for Multivariate Optical Elements," Applied Optics, vol. 42, Issue 10, 2004, pp. 1833-1838.
Soyemi et al., "Design and Testing of a Multivariate Optical Element: The First Demonstration of Multivariate Optical Computing for Predictive Spectroscopy," Analytical Chemistry, 2001, vol. 73, No. 6, pp. 1069-1079.

* cited by examiner

OPTICAL DESIGN TECHNIQUES FOR PROVIDING FAVORABLE FABRICATION CHARACTERISTICS

This application is a National Stage entry of and claims priority to International Application No. PCT/US2013/026894, filed on Feb. 20, 2013.

BACKGROUND

The present invention relates to optical computing devices and, more particularly, to optical design techniques that provide favorable fabrication characteristics for optical elements used in optical computing devices.

Optical computing devices, also commonly referred to as "opticoanalytical devices," can be used to analyze and monitor a substance in real time. Such optical computing devices will often employ a processing element that optically interacts with the substance to determine quantitative and/or qualitative values of one or more physical or chemical properties of the substance. The processing element may be, for example, an integrated computational element (ICE), also known as a multivariate optical element (MOE), which is essentially an optical interference filter that can be designed to operate over a continuum of wavelengths in the electromagnetic spectrum from the UV to mid-infrared (MIR) ranges, or any sub-set of that region. Electromagnetic radiation that optically interacts with the ICE is changed so as to be readable by a detector, such that an output of the detector can be correlated to the physical or chemical property of the substance being analyzed.

One exemplary type of ICE includes a plurality of layers consisting of various materials whose index of refraction and size (e.g., thickness) may vary between each layer. An ICE design refers to the number and thickness of the respective layers of the ICE component. The layers may be strategically deposited and sized so as to selectively pass predetermined fractions of electromagnetic radiation at different wavelengths configured to substantially mimic a regression vector corresponding to a particular physical or chemical property of interest. Accordingly, an ICE design will exhibit a transmission function that is weighted with respect to wavelength. After the electromagnetic radiation from a light source interacts with a sample and ICE, the output light is conveyed to an optical transducer or detector. The total intensity measured by the detector is related to the physical or chemical property of interest for the substance.

It has been found, however, that the resulting transmission function for some ICE designs may change or shift based on errors in fabricating the individual ICE components. For example, during fabrication of an ICE component, slight errors may be made while depositing one or more of its layers. While some errors in a particular layer might cause a large shift in the transmission spectra of the ICE component as a whole, such errors may not be detrimental to the prediction performance of the ICE component. On the other hand, errors on another layer may cause only a slight spectral shift in the transmission profile, but this small shift may be significant with respect to prediction performance. It may be advantageous to determine which ICE designs may have hypersensitive layers for which extra care should be taken during the fabrication process to ensure minimal layer error.

SUMMARY OF THE INVENTION

The present invention relates to optical computing devices and, more particularly, to optical design techniques that provide favorable fabrication characteristics for optical elements used in optical computing devices.

In some embodiments, a method of evaluating an optical element for fabrication is disclosed. The method may include randomizing a design thickness of each layer of a desired integrated computational element (ICE) design to simulate a fabrication error in each layer, thereby generating a plurality of randomized ICE designs, calculating a standard error of calibration for each randomized ICE design, correlating the standard error of calibration between a given layer of the desired ICE design and the fabrication error of each corresponding layer of each randomized ICE design, and ranking the plurality of layers of the desired ICE design based on the sensitivity to changes in the standard error of calibration.

In other embodiments, a method of evaluating and fabricating an optical element is disclosed. The method may include altering a design thickness of each layer of a desired integrated computational element (ICE) design to simulate a fabrication error in each layer, thereby generating a plurality of randomized ICE designs, calculating a standard error of calibration between each randomized ICE design and the desired ICE design, correlating the standard error of calibration between a given layer of the desired ICE design and the fabrication error of each corresponding layer of each randomized ICE design, ranking the plurality of layers of the desired ICE design based on the sensitivity to changes in the standard error of calibration, and depositing each sensitive layer with increased accuracy and precision.

The features and advantages of the present disclosure will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
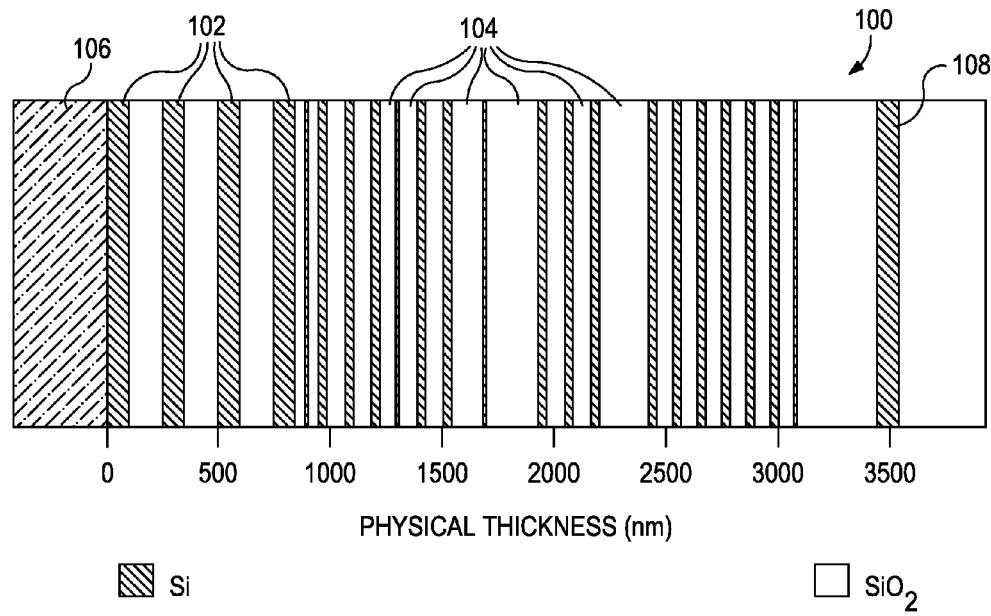
FIG. 1 illustrates an exemplary integrated computation element, according to one or more embodiments.

The present invention relates to optical computing devices and, more particularly, to optical design techniques that provide favorable fabrication characteristics for optical elements used in optical computing devices.

The present disclosure facilitates the evaluation of desired integrated computational element (ICE) designs to determine how layer errors due to physical fabrication methods affect chemometric predictability. Instead of calculating the mean squared error (MSE) from the spectral changes of the ICE design, the present disclosure uses the standard error of calibration (SEC). As a result, the methods disclosed herein may be able to determine which layers of a desired ICE design would be more sensitive to fabrication errors and would therefore detrimentally impact the overall SEC of a batch of the desired ICE design. Once an operator knows which layers are more sensitive to fabrication errors than others, additional care and precision may be taken in physically depositing those sensitive layers.

The methods disclosed herein may help an operator determine if a particular desired ICE design contains hypersensitive layers in which small deposition layer errors may be capable of degrading chemometric predictability to a point where the desired ICE design would be rendered useless or otherwise ineffective for its intended purpose. Moreover, using the methods disclosed herein, an operator may be able to intelligently determine which batch of a desired ICE design would be more desirable than another due to a lower average batch SEC. Therefore, the methods disclosed herein may also help an operator determine which desired ICE design is more preferred over other desired ICE designs.

The disclosed systems and methods may be suitable for designing, evaluating, and fabricating ICE components for use in the oil and gas industry which oftentimes deploys optical computing devices in environments exhibiting extreme conditions. It will be appreciated, however, that the various disclosed systems and methods are equally applicable to designing and fabricating ICE components for use in other technology fields including, but not limited to, the food and drug industry, industrial applications, mining industries, or any field where it may be advantageous to determine in real-time or near real-time a characteristic of a specific substance, but where the environmental factors, such as temperature, pressure, and humidity, have a critical impact in monitoring applications.

As used herein, the term "characteristic" refers to a chemical, mechanical, or physical property of a substance. A characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be monitored with the optical computing devices described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, combinations thereof, state of matter (solid, liquid, gas, emulsion, mixtures, etc), and the like.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation associated with a substance and produce an output of electromagnetic radiation from a processing element arranged within the optical computing device. The processing element may be, for example, an integrated computational element (ICE), also known as a multivariate optical element (MOE). The electromagnetic radiation that optically interacts with the processing element is changed so as to be readable by a detector, such that an output of the detector can be correlated to a particular characteristic of the substance. The output of electromagnetic radiation from the processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid, for example via fluorescence, luminescence, Raman, Mie, and/or Raleigh scattering, can also be monitored by optical computing devices.

As used herein, the term "optically interact" or variations thereof refers to the reflection, transmission, scattering, diffraction, or absorption of electromagnetic radiation either on, through, or from one or more processing elements (i.e., ICE or MOE components) or a substance being analyzed by the processing elements. Accordingly, optically interacted light refers to electromagnetic radiation that has been reflected, transmitted, scattered, diffracted, or absorbed by, emitted, or re-radiated, for example, using a processing element, but may also apply to interaction with a substance.

As mentioned above, the processing element used in the above-defined optical computing devices may be an integrated computational element (ICE). In operation, an ICE is capable of distinguishing electromagnetic radiation related to a characteristic of interest of a substance from electromagnetic radiation related to other components of the substance. Referring to FIG. 1, illustrated is an exemplary ICE 100, according to one or more embodiments. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples of materials might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation, and may be able to detect a sample substance. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths. It should be understood that the exemplary ICE 100 in FIG. 1 does not in fact represent any particular characteristic of a given substance, but is provided for purposes of illustration only. Consequently, the number of layers 102, 104 and their relative thicknesses, as shown in FIG. 1, bear no correlation to any particular characteristic. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the given substance being analyzed.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices. Further information regarding the structures and design of exemplary ICE elements is provided in *Applied Optics*, Vol. 35, pp. 5484-5492 (1996) and Vol. 29, pp. 2876-2893 (1990), which are hereby incorporated by reference.

The weightings that the layers 102, 104 of the ICE 100 apply at each wavelength are set to the regression weightings described with respect to a known equation, or data, or spectral signature. When electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. The ICE 100 may be configured to perform the dot product of the electromagnetic radiation received by the ICE 100 and the wavelength dependent transmission function of the ICE 100. The wavelength dependent transmission function of the ICE 100 is dependent on the layer material refractive index, the number of layers 102, 104 and the layer thicknesses. The ICE 100 transmission function is then analogous to a desired regression vector derived from the solution to a linear multivariate problem targeting a specific component of the sample being analyzed. As a result, the output light intensity of the ICE 100 is related to the characteristic or analyte of interest.

The optical computing devices employing such an ICE 100 may be capable of extracting the information of the spectral fingerprint of multiple characteristics or analytes within a substance and converting that information into a detectable output regarding the overall properties of the substance. That is, through suitable configurations of the optical computing devices, electromagnetic radiation associated with characteristics or analytes of interest in a substance can be separated from electromagnetic radiation associated with all other components of the substance in order to estimate the properties of the substance in real-time or near real-time. Further details regarding how the exemplary ICE 100 is able to distinguish and process electromagnetic radiation related to the characteristic or analyte of interest are described in U.S. Pat. Nos. 6,198,531; 6,529,276; and 7,920,258, incorporated herein by reference in their entirety.

Before an ICE component is physically fabricated for use one or more theoretical designs of the ICE component are typically generated. Such theoretical designs may be generated using, for example, a computer-based software program or design suite that may be stored on a computer-readable medium containing program instructions configured to be executed by one or more processors of a computer system. The design suite may be configured to generate several theoretical ICE designs, each being configured or otherwise adapted to detect a particular characteristic or analyte of interest.

In some embodiments, the design suite may commence the design process by generating a single theoretical ICE design that has a random number of layers and/or a random layer thickness for each layer. The design suite may then proceed to optimize the number of layers and/or layer thicknesses of the ICE design based on several "figures of merit" or performance criteria. Such performance criteria may include, but are not limited to, minimum prediction error, standard error of calibration (SEC), standard error of performance (SEP), sensitivity, slope of the calibration curve, signal-to-noise ratio, and mean transmission value corresponding to the particular characteristic or analyte of interest. During this optimization process, the design suite may be configured to vary layer thicknesses and/or remove layers until several designs of the ICE component are generated that meet one or more minimum criteria for predicting the analyte of interest. Several thousands of varying ICE designs may be generated from the theoretical ICE component during this stage.

Once these theoretical ICE component designs are generated, they may be sorted by the design suite based on, for example, prediction error and signal. In some cases, the various ICE designs may be sorted based on their overall SEC (i.e., chemometric predictability) as tested against a known value for the characteristic or analyte of interest. For example, the SEC for each ICE design may be calculated by taking the square root of the sum of squares between the known value for the analyte of interest and the predicted value as derived from the transmission spectrum of the particular ICE design. This is accomplished for each theoretical ICE design by calculating its respective transmission spectrum and applying that transmission spectrum to the known data set of the analyte of interest.

In some embodiments, the design suite may be configured to iterate and/or optimize layer thicknesses and numbers until reaching a reasonable SEC for one or more of the theoretical ICE designs. The resulting SEC for each ICE design is indicative of how good of a predictor the particular ICE component will be for the analyte of interest. In some embodiments, ICE designs exhibiting an SEC of 2.00 or less, for example, may be considered "predictive" and ICE designs exhibiting an SEC of greater than 2.00 may be considered "non-predictive." In other embodiments, the resulting SEC value that determines whether an ICE design will be considered predictive or not may be greater or less than 2.00, without departing from the scope of the disclosure. Those ICE designs that are ultimately considered non-predictive may be removed from consideration either by an operator or by software instructions carried out by the design suite.

Once a predictive or desired ICE design is ultimately selected for fabrication, the design may then be loaded into a fabrication computer program configured to instruct a fabrication machine or module to physically create the ICE component. Similar to the design suite, the fabrication computer program software may be stored on a computer-readable medium containing program instructions configured to be executed by one or more processors of a computer system. The fabrication computer program may be configured to receive or otherwise download the specifications for the desired ICE design, as generated by the design suite, and physically create a corresponding ICE component by methodically depositing the various layers of the ICE component to the specified layer thicknesses.

During the fabrication process, however, physical errors can often be made that may have the effect of decreasing the predictability of an otherwise predictive ICE design. Such errors can include, for example, inadvertently depositing the material of one or more of the layers to a thickness that deviates from the designed thickness specification. According to embodiments of the disclosure, predictive or desired ICE designs may be analyzed or otherwise evaluated prior to fabrication in order to reliably select an ICE design that can be fabricated with reproducible predictability and that will otherwise provide a reproducible transmission profile. Such analysis and evaluation may prove advantageous in the selection of more robust and predictive ICE designs for fabrication and for fabrication decisions.

Figure 2:
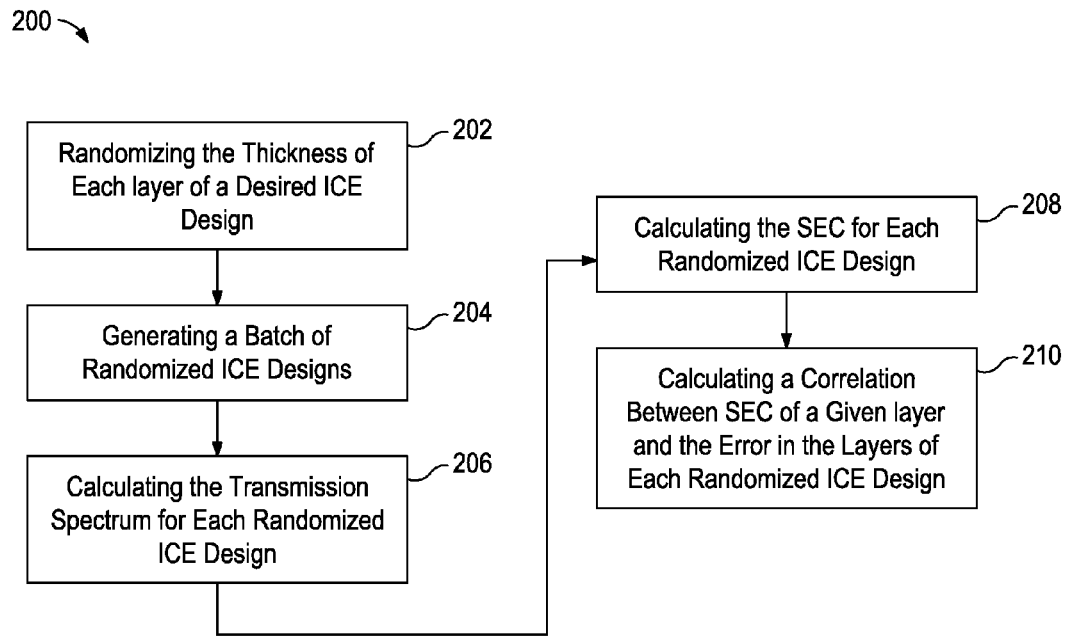
FIG. 2 illustrates a schematic flowchart of a method of evaluating an ICE design for fabrication, according to one or more embodiments.

Referring to FIG. 2, illustrated is a schematic flowchart providing an exemplary method 200 of evaluating an ICE design for fabrication, according to one or more embodiments. Portions of the method 200 will be described with reference to the exemplary desired ICE design shown in Table 1 below. As indicated in Table 1, the desired ICE design encompasses a total of eight layers, and each layer has a different design layer thickness as determined by the exemplary design process generally described above. It should be noted that the exemplary desired ICE design in Table 1 is merely used for illustrative purposes and therefore should not be considered limiting to the scope of this disclosure.

TABLE 1

Exemplary ICE Design

| Layer # | Thickness (nm) |
|---|---|
| 1 | 905.09 |
| 2 | 502.63 |
| 3 | 246.69 |
| 4 | 709.09 |
| 5 | 99.46 |
| 6 | 273.71 |
| 7 | 1206.40 |
| 8 | 1004.62 |

In some embodiments, the method 200 may include randomizing or otherwise altering the thickness of each layer of the desired ICE design, as at 202. Randomizing or altering the thickness of each layer may simulate typical fabrication errors that may occur during the deposition process of physically fabricating each layer of the desired ICE design. In some embodiments, the randomized error applied to each layer could be entirely "random," as generated or otherwise configured by the fabrication computer program or another computational or physical device designed to generate a sequence of thickness errors that lack any pattern.

In other embodiments, however, the randomized error applied to each layer may follow a predetermined error iteration that changes the design thickness of each layer by a known thickness variance or certain percentage of the design thickness for each layer (e.g., either an increase or decrease in layer thickness). For example, the design layer thickness of each layer of the desired ICE design may be varied by thickness variances of 1 nanometer (nm), 5 nm, 10 nm, etc., combinations thereof, fractions thereof, and the like. Similarly, the design thickness of each layer of the desired ICE design may be varied by 0.1% of the design layer thickness, 0.5% of the design layer thickness, 1.0% of the design layer thickness, 5.0% of the design layer thickness, etc., combinations thereof, fractions thereof, and the like.

As will be appreciated, this process may result in the generation of a plurality or "batch" of randomized ICE designs, as at 204, where each randomized ICE design in the batch may have each layer thereof varied with either a random or predetermined error variation. The resulting batch of randomized ICE designs may include any number of randomized ICE designs as set by an operator or computerized system. In some embodiments, for example, a batch of randomized ICE designs may include 100 randomized ICE designs. In other embodiments, a batch of randomized ICE designs may include 500, 1,000, or 10,000 randomized ICE designs, without departing from the scope of the disclosure.

Figure 3:
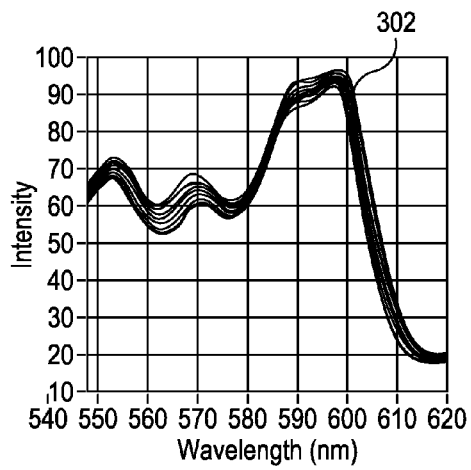
FIG. 3 illustrates a plot that depicts a transmission spectrum for an exemplary randomized ICE design.

The method 200 may then proceed by calculating the transmission spectrum for each of the randomized ICE designs, as at 206. As known by those skilled in the art, such transmission spectra may be calculated or otherwise generated using a computer system, such as a computer system able to run the fabrication software program described above, or another suitable computing program. Referring to FIG. 3, illustrated is a plot 300 that depicts transmission spectra 302 for an exemplary randomized ICE design. Specifically, the transmission spectra 302 correspond to a randomized ICE design that has been randomized from the desired ICE design of Table 1 above. As discussed below, by using the transmission spectra 302 of the randomized ICE design, it may be possible to evaluate each individual layer thereof in an effort to determine which layers are more sensitive than others to fabrication error variations.

Referring again to FIG. 2, the method 200 may proceed by calculating the chemometric SEC (or standard error of prediction (SEP)) for each randomized ICE design, as at 208. In at least one embodiment, the chemometric SEC for each randomized ICE design may be calculated by taking the square root of the sum of squares between the known value for the analyte of interest and the predicted value as derived from the transmission spectrum of the desired ICE design. This is accomplished for each randomized ICE design by calculating its respective transmission spectrum and applying that transmission spectrum to the known data set of the analyte of interest. Such a calculation of an entire randomized ICE design in view of the original (error-free) desired ICE design may help determine how well a particular randomized ICE design will perform with the randomized errors applied to each layer.

The method 200 may then include correlating the SEC (or SEP) between a given layer and the error in the layers of each randomized ICE design, as at 210. More particularly, the SEC may be calculated for each layer between the error in each layer of each randomized ICE design and the resulting SEC degradation as compared with the corresponding layers of the desired (error-free) ICE design (Table 1). In some embodiments, a correlation coefficient may be determined or otherwise obtained therefrom for each layer of the desired ICE design, and the correlation coefficient may be directly proportional to how sensitive that layer may be to fabrication error. The results of such calculations may prove advantageous in determining which layers of the desired ICE design are more sensitive to fabrication errors and would therefore result in large shifts in the transmission profile and decreases in overall predictability.

Figure 4:
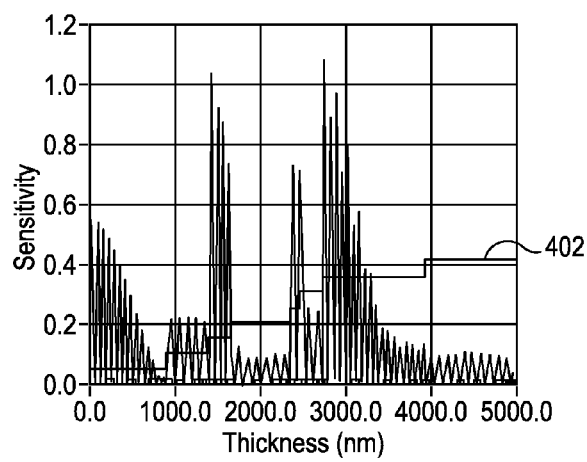
FIG. 4 illustrates a sensitivity plot depicting the sensitivity of each layer of the randomized ICE design of FIG. 3.

Referring to FIG. 4, with continued reference to FIG. 3, illustrated is a sensitivity plot 400 depicting the sensitivity of each layer of the randomized ICE design of FIG. 3. The sensitivity plot 400 may be generated by comparing the transmission spectra 302 of FIG. 3 with the original transmission spectra of the desired (error-free) ICE design of Table 1, and the resulting peaks and valleys shown in the sensitivity plot 400 indicate sensitivity magnitude of each layer as corresponding to the respective error applied thereto.

A demarcation line 402 in the sensitivity plot 400 identifies a series of "steps" corresponding to each contiguous layer of the randomized ICE design. Specifically, as moving left to right in the sensitivity plot 400, each step extends across the respective thickness of each contiguous layer of the randomized ICE design, as indicated on the x-axis. For example, the first step (far left) of the demarcation line 402 corresponds to the first layer of the randomized ICE design and encompasses a thickness of about 900 nm. The second step (to the right of the first step) of the demarcation line 402 corresponds to the second layer of the randomized ICE design and has a thickness of about 500 nm. The remaining steps (sequentially connected to the right of the second step) of the demarcation line 402 correspond to the remaining layers of the randomized ICE design, respectively, and otherwise indicate the thickness of each layer, as represented on the x-axis. Accordingly, the overall thickness of the randomized ICE design is about 5000 nm.

As can be seen in the sensitivity plot 400, layers three, five, and seven of the particular randomized ICE design appear to be more sensitive to the applied error than the remaining layers. Moreover, layers four and eight appear to be the least sensitive to the applied errors than the remaining layers. Similar sensitivity plots and determinations may be made for each randomized ICE design of the batch of randomized ICE designs. A statistical analysis of the results from each sensitivity plot corresponding to each randomized ICE design, may indicate which layers of the desired ICE design (Table 1) may be more sensitive to fabrication errors, thereby providing the correlation or corresponding correlation coefficient between the layer error and the resulting SEC degradation. Results of such an analysis are depicted in FIG. 5.

Figure 5:
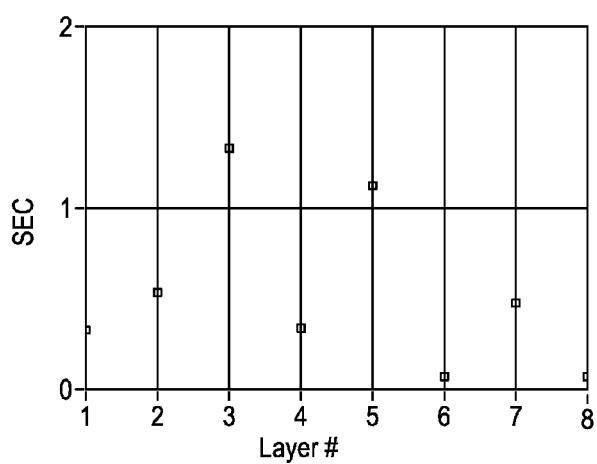
FIG. 5 illustrates a fabrication sensitivity plot corresponding to a desired ICE design.

Referring to FIG. 5, with continued reference to FIGS. 3 and 4, illustrated is a fabrication sensitivity plot 500 corresponding to the desired ICE design of Table 1. In particular, the plot 500 provides SEC on the y-axis as a function of each layer of the desired ICE design, as shown on the x-axis. Each point in the plot 500 represents an average SEC value for the indicated layer of the desired ICE design as derived from the corresponding layers of each randomized ICE design. In other words, the sensitivity plots for each randomized ICE design (i.e., similar to the sensitivity plot 400 of FIG. 4) were combined and the sensitivity of each layer in view of the applied error was averaged in order to determine the average sensitivity of each respective layer. From the average sensitivity of each layer of the randomized ICE designs, the average SEC of the respective layers could be determined and otherwise depicted in the fabrication sensitivity plot 500.

As shown in the plot 500, the sixth and eight layers report having the least effect on SEC as opposed to the remaining layers. In other words, fabrication errors in the sixth and eight layers will likely have little or negligible detrimental impact on the overall SEC of the desired ICE design. On the other hand, the third and fifth layers report having the most effect on SEC as opposed to the remaining layers. As a result, fabrication errors in the third and fifth layers will likely have a greater negative impact on the overall SEC of the desired ICE design than the remaining layers. Accordingly, the plurality of layers of the desired ICE design have been effectively ranked based on the sensitivity to changes in the standard error of calibration. In accordance with such ranking, the third and fifth layers of the desired ICE design may be characterized or otherwise treated as sensitive or hypersensitive layers of the desired ICE design.

Once an operator knows which of the layers of a desired ICE design will be more sensitive to fabrication errors than others, the care with which each layer is deposited may be set depending on the effect that a particular layer may have on the final chemometric predictability (SEC or SEP). In some embodiments, for example, the deposition of more sensitive layers may be set by slowing the deposition rate and thereby ensuring accurate and precise deposition of such layers during the fabrication process. In other embodiments, or otherwise in addition thereto, the deposition of more sensitive layers may be set by programming or otherwise undertaking various optical measurements (e.g., analyzing the transmission profile) during the fabrication process of such sensitive layers to ensure that the deposition thickness does not overshoot or otherwise undershoot the original design parameters for the desired ICE design. For instance, optical measurements may be taken at predetermined deposited thicknesses of the sensitive layers, such as by taking optical measurements at 50%, 60%, 70%, 80%, 90%, 95%, etc. of the total layer deposition. Those skilled in the art will readily recognize that the optical measurements may be taken at other percentages of the total layer deposition, without departing from the scope of the disclosure. In other words, additional precision, accuracy, or focus on the part of the operator may be necessary or otherwise recommended in setting the layers that are more susceptible to causing SEC degradation.

The methods disclosed herein may also prove advantageous in helping an operator make fabrication decisions. For instance, the disclosed methods may help an operator determine if a particular desired ICE design contains hypersensitive layers in which small deposition layer errors may be capable of degrading chemometric predictability to a point where the desired ICE design would be rendered useless or otherwise ineffective for its intended purpose. In such cases, the operator may be able to intelligently determine if a desired ICE design is a viable design in terms of reproducible predictability or its ability to provide a reproducible transmission profile. Desired ICE designs that are determined to be non-viable may be discarded entirely prior to expending the time and resources in fabricating the same.

The methods disclosed herein may also help an operator determine which desired ICE design is more preferred over other desired ICE designs. For example, the final fabricated batch of ICE components following a manufacturing run will likely contain ICE components that are predictive, despite exhibiting spectral shifts attributable to fabrication layer errors. Using the presently disclosed methods, however, the operator may be able to intelligently determine which batch of a desired ICE design would be more desirable than another due to a lower average batch SEC. As a result, the batch of the chosen desired ICE design will result in a higher yield of predictive ICE components.

Those skilled in the art will readily appreciate that the methods described herein, or large portions thereof, may be automated at some point such that a computerized system may be programmed to design, predict, and fabricate ICE components that are more robust for fluctuating extreme environments. Computer hardware used to implement the various methods and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), electrically erasable programmable read only memory (EEPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method of fabricating an optical element, comprising:
    randomizing a design thickness of each layer of a desired integrated computational element (ICE) design to simulate a fabrication error in each layer, thereby generating a plurality of randomized ICE designs;
    calculating a standard error of calibration for each randomized ICE design;
    correlating the standard error of calibration for each randomized ICE design with the fabrication error of each corresponding layer of each randomized ICE design;
    ranking the plurality of layers of the desired ICE design based on a sensitivity of the standard error of calibration to the fabrication error of each corresponding layer; and
    depositing at least one of higher ranking layer in the plurality of layers of the desired ICE design on an optical substrate at a slower deposition rate compared to at least one lower ranking layer.

2. The method of claim 1, wherein randomizing the design thickness of each layer comprises randomly varying the thickness of each layer.

3. The method of claim 1, wherein randomizing the design thickness of each layer comprises varying the thickness of each layer by a predetermined amount.

4. The method of claim 3, wherein the predetermined amount comprises a known thickness variance.

5. The method of claim 3, wherein the predetermined amount comprises a percentage of a design thickness for each layer.

6. The method of claim 1, wherein calculating the standard error of calibration further comprises:
    calculating transmission spectra for each of the randomized ICE designs; and
    calculating the square root of the sum of squares between a known value for an analyte of interest and a predicted value as derived from a transmission spectra of the desired ICE design.

7. The method of claim 1, further comprising removing the desired ICE design from fabrication consideration when the desired ICE design contains a layer that renders the desired ICE design non-predictive.

8. The method of claim 1, wherein the desired ICE design is a first desired ICE design, the method further comprising selecting the first desired ICE design for fabrication over a second desired ICE design based on a lower average batch standard error of calibration.

9. The method of claim 1, further including the step of determining whether each randomized ICE design is predictive or non-predictive, based on the standard error of calibration.

10. The method of claim 1, further comprising selecting at least one sensitive layer from the plurality of layers based on the ranking of the plurality of layers.

11. A non-transitory computer readable medium programmed with computer executable instructions therein for performing the method of claim 2.

12. A method of fabricating an optical element, comprising:
    altering a design thickness of each layer of a desired integrated computational element (ICE) design to simulate a fabrication error in each layer, thereby generating a plurality of altered ICE designs;

calculating a standard error of calibration for each altered ICE design;

correlating the standard error of calibration for each altered ICE design with the fabrication error of each corresponding layer of each altered ICE design;

ranking the plurality of layers of the desired ICE design based on a sensitivity of the standard error of calibration to the fabrication error of each corresponding layer; and depositing at least one higher ranking layer in the plurality of layers of the desired ICE design on an optical substrate at a slower deposition rate compared to at least one lower ranking layer.

13. The method of claim 12, wherein depositing at least one higher ranking layer in the plurality of layers comprises taking an optical measurement during the deposition of the at least one higher ranking layer.

14. The method of claim 12, further comprising undertaking a plurality of optical measurements of the at least one higher ranking layer at predetermined deposited thicknesses during deposition.

15. The method of claim 14, further comprising undertaking optical measurements during deposition of the at least one higher ranking layer at predetermined percentages of a total layer deposition.

16. The method of claim 15, wherein the predetermined percentages comprise about 50%, about 60%, about 70%, about 80%, about 90%, and about 95% of the total layer deposition.

17. The method of claim 12, wherein correlating a standard error of calibration for each of the plurality of altered ICE design comprises forming a sensitivity plot for each of the plurality of altered ICE designs and performing a statistical analysis of the results in the sensitivity plot for each of the plurality of altered ICE designs to find a sensitivity to fabrication errors of the desired ICE design.

18. The method of claim 12, wherein altering the design thickness of each layer comprises varying the thickness of each layer by a predetermined amount.

19. The method of claim 18, wherein the predetermined amount comprises a known thickness variance.

20. The method of claim 18, wherein the predetermined amount comprises a percentage of a design thickness for each layer.

21. The method of claim 12, further comprising removing the desired ICE design from fabrication consideration when the desired ICE design contains a layer that renders the desired ICE design non-predictive.

22. The method of claim 12, wherein the desired ICE design is a first desired ICE design, the method further comprising selecting the first desired ICE design for fabrication over a second desired ICE design based on a lower average batch standard error of calibration.

23. The method of claim 12, wherein depositing the at least one higher ranking layer comprises reducing a deposition thickness error.

* * * * *